(12) United States Patent
Hong et al.

(10) Patent No.: US 6,423,797 B1
(45) Date of Patent: Jul. 23, 2002

(54) ANTI-REFLECTIVE COATING POLYMERS FROM P-TOSYLMETHYLACRYLAMIDE AND PREPARATION METHOD

(75) Inventors: Sung-Eun Hong; Min-Ho Jung; Ki-Ho Baik, all of Gyunggi-do (KR)

(73) Assignee: Hyundai Electronics Industries Co., Ltd. (KR)

( * ) Notice: Subject to any disclaimer, the term of this patent is extended or adjusted under 35 U.S.C. 154(b) by 167 days.

(21) Appl. No.: 09/603,561

(22) Filed: Jun. 23, 2000

(30) Foreign Application Priority Data

Jun. 26, 1999 (KR) .............................. 99-24470

(51) Int. Cl.[7] .............................. C08F 2/06; C08F 24/00; C08F 12/30
(52) U.S. Cl. ..................... 526/204; 526/219.6; 526/273; 526/287
(58) Field of Search .............................. 526/204, 219.6, 526/227, 273, 287

(56) References Cited

U.S. PATENT DOCUMENTS

| | | | |
|---|---|---|---|
| 4,424,270 A | 1/1984 | Erdmann et al. | 430/166 |
| 4,822,718 A | 4/1989 | Latham et al. | 430/271 |
| 5,674,648 A | 10/1997 | Brewer et al. | 430/18 |

FOREIGN PATENT DOCUMENTS

| | | | |
|---|---|---|---|
| EP | 0 277 038 | 1/1988 | |
| WO | WO 00/01752 | 1/2000 | |

*Primary Examiner*—Christopher Henderson
(74) *Attorney, Agent, or Firm*—Townsend and Townsend and Crew LLP

(57) ABSTRACT

The present invention relates to organic anti-reflective coating polymers suitable for use in manufacturing a semiconductor device using a photolithography process for forming ultrafine-patterns with a 193 nm ArF beam, and preparation methods therefor. Anti-reflective coating polymers of the present invention contain a monomer having a phenyl group and amide linkage with high light absorbency at the 193 nm wavelength. When the polymers of the present invention are used in an anti-reflective coating in a photolithography process for forming ultrafine-patterns, the polymers eliminate the standing waves caused by changes in the thickness of the photoresist layer, by the spectroscopic property of the lower layers of the semiconductor wafer and by changes in CD due to diffractive and reflective light originating from the lower layer, thereby resulting in the stable formation of ultrafine-patters suitable for 64 M, 256 M, 1 G, 4 G and 16 G DRAM semiconductor devices and a great improvement in the production yield.

The present invention also relates to anti-reflective compositions containing these polymers, anti-reflective coatings formed from these compositions and semiconductor devices containing these anti-reflective coatings, as well as preparation methods therefor.

35 Claims, No Drawings

ANTI-REFLECTIVE COATING POLYMERS FROM P-TOSYLMETHYLACRYLAMIDE AND PREPARATION METHOD

CROSS-REFERENCES TO RELATED APPLICATIONS

This application is related to Korean Patent Application No. 1999-24470 filed Jun. 26, 1999, and takes priority from that date.

BACKGROUND OF THE INVENTION

1. Field of the Invention

The present invention relates to organic polymers suitable for use in anti-reflective coatings on semiconductor devices, and methods for preparing them. More specifically, the polymers of the present invention can be used to form a layer which prevents the reflection of light from lower layers coated on a semiconductor chip when photolithography processes using 193 nm (ArF) wavelengths are employed during the manufacture of 64 M, 256 M, 1 G, 4 G and 16 G DRAM semiconductor devices. Anti-reflective coatings comprising polymers of the present invention also eliminate the standing wave effect when an ArF beam is used, and reflection/diffraction caused by changes in the thickness of the photoresist layer itself. The present invention also relates to anti-reflective compositions containing these polymers and anti-reflective coatings formed from these compositions, as well as preparation methods therefor.

2. Description of the Prior Art

In photolithography processes for forming ultrafine-patterns during the manufacture of semiconductors, it is unavoidable to have reflective notching of the standing wave of the exposing radiation. This effect is due to the spectroscopic properties of the lower layers coated on the semiconductor wafer, changes in the photoresist layer and variations in the critical dimension (CD) due to diffracted and reflected light from the lower layer. Therefore, it has been suggested that a layer, called an anti-reflective coating, be introduced into the semiconductor device to prevent the reflection of light from the lower layers. This anti-reflective coating usually comprises an organic material that absorbs light in the wavelength range of the light beam source used in the lithography process.

Anti-reflective coatings are categorized into inorganic and organic anti-reflective coatings depending on the coating materials used, or into light-absorbing and light-interfering coatings depending on the mechanism.

An inorganic anti-reflective coating is used mainly in the process of ultrafine-pattern formation using i-line radiation with a wavelength of 365 nm. TiN and amorphous carbon have been widely used in light-absorbing coatings, and SiON has been used in light-interfering coatings.

Inorganic SiON has been used for anti-reflective coatings in ultrafine-pattern formation processes using a KrF beam. A recent trend has been to try to use organic compounds in an anti-reflective coating. Based on knowledge to date, the following are prerequisites for an adequate organic anti-reflective coating:

First, during the pattern formation process, the photoresist must not be peeled from the substrate by dissolving in the solvent used in the organic anti-reflective coating. For this reason, the organic anti-reflective coating needs to be designed to form a cross-linked structure, and must not produce chemicals as a by-product.

Second, acid or amine compounds must not migrate in or out of the anti-reflective coating. This is because there is a tendency for undercutting at the lower side of the pattern if an acid migrates, and for footing if a base such as an amine migrates.

Third, the anti-reflective coating must have a faster etching speed compared to the photoresist layer so that the etching process can be performed efficiently by utilizing the photoresist layer as a mask.

Fourth, the anti-reflective coating must function with a minimal thickness.

Up to now, suitable anti-reflective coatings have not been developed for use in processes for forming an ultrafine-pattern using an ArF beam. Furthermore, since there is no known inorganic anti-reflective coating that controls the interference from a 193 nm light source, the use of organic chemicals in anti-reflective coatings is currently being studied.

Therefore, it is desirable to use and develop organic anti-reflective coatings that absorb light strongly at specific wavelengths to prevent the standing wave effect and light reflection in lithography processes, and to eliminate the rear diffraction and reflected light from the lower layers.

SUMMARY OF THE INVENTION

The present invention provides novel chemical compounds suitable for use in anti-reflective coatings in photolithography processes for forming ultrafine-patterns using 193 nm (ArF) and 248 nm (KrF) light beams in the manufacture of semiconductor devices.

The present invention further provides preparation methods for chemical compounds to be used in anti-reflective coatings.

The present invention also provides anti-reflective coating compositions containing the above-mentioned compounds and preparation methods thereof. The present invention also provides anti-reflective coatings formed by using the above-mentioned anti-reflective composition, and methods for the formation thereof.

The polymers of the present invention comprise a monomer with a phenyl group and an amide linkage having high absorbance at 193 nm, so that the polymer resin absorbs 193 nm wavelength light. A cross-linking mechanism using a ring opening reaction is introduced into preferred polymer resins of the invention by adding another monomer having an epoxy structure, so that a cross-linking reaction takes place when coatings of the polymer resins are "hard baked", i.e., heated at a temperature of 100–300° C. for 10–1,000 seconds. Accordingly, a great improvement can be effected in the formation, tightness and dissolution properties of the anti-reflective coatings using polymers of the present invention. Particularly, maximal cross-linking reaction efficiency and storage stability are realized by the present invention. The anti-reflective coating resins of the present invention have superior solubility in all hydrocarbon solvents, in order to form a coating composition, yet are of such high solvent resistance after hard baking that they are not dissolved in any solvent at all. These advantages allow the resins to be coated without any problem to form an anti-reflective coating which prevents undercutting and footing problems when images are formed on the overlying photosensitive layer. Furthermore, coatings made of the acrylate polymers of the invention are higher in etch rate than the photosensitive film coatings, thereby improving the etch selection ratio therebetween.

DETAILED DESCRIPTION OF THE INVENTION

Preferred copolymer resins according to the present invention are represented by the following general formula

1:

(general formula 1)

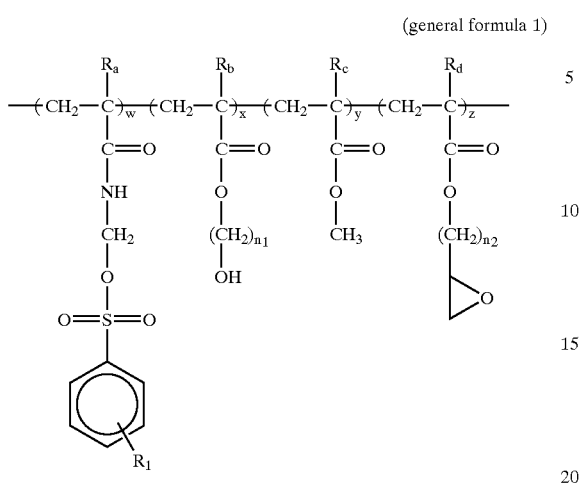

wherein, $R_a$, $R_b$, $R_c$ and $R_d$ each represents hydrogen or methyl; $R_1$ represents hydrogen, hydroxy, a substituted or non-substituted straight or branched $C_1$–$C_5$ alkyl, cycloalkyl, alkoxyalkyl or cycloalkoxyalkyl; w, x, y and z each represents mole fraction of 0.01–0.99; and $n_1$ and $n_2$ each represents an integer of 1 to 4.

and by the following general formula 2:

(general formula 2)

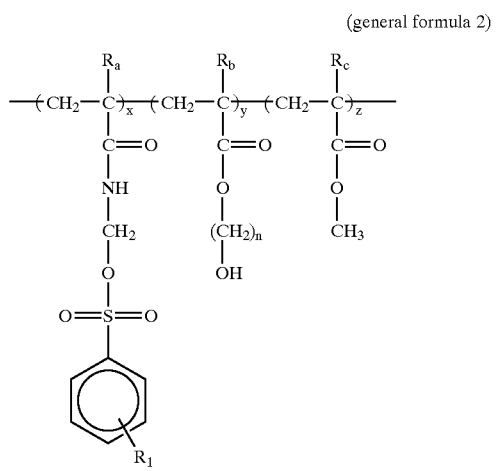

wherein, $R_a$, $R_b$, and $R_c$ each represents hydrogen or methyl; $R_1$ represents hydrogen, hydroxy, a substituted or non-substituted straight or branched $C_1$–$C_5$ alkyl, cycloalkyl, alkoxyalkyl or cycloalkoxyalkyl; x, y and z each represents mole fraction of 0.01–0.99; and n represents an integer of 1 to 4.

The polymer resins of the present invention are particularity suitable for use in organic anti-reflective coatings since they comprise a monomer having a phenyl group and amide linkage having excellent absorbency of 193 nm wavelenth radiation. Preferred monomers comprise a p-tosylalkylacrylamide-type monomer of the following chemical formula 3:

(general formula 3)

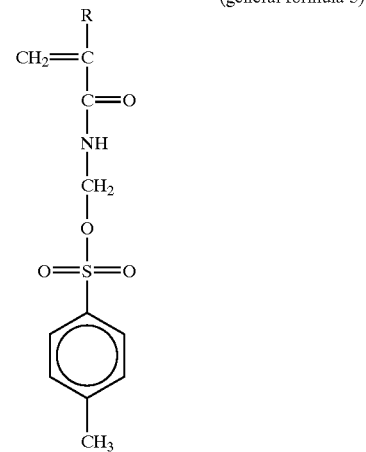

wherein R is hydrogen or methyl.

The polymers represented by general formula 1 can be prepared in accordance with the reaction equation 1 set forth below, wherein a p-tosylalkylacrylamide-type monomer, an hydroxyalkylacrylate-type monomer, a methylacrylate-type monomer and a glycidylacrylate-type monomer are polymerized with the aid of an initiator in a solvent. Each of the monomers has a mole fraction ranging from 0.01 to 0.99.

(reaction equation 1)

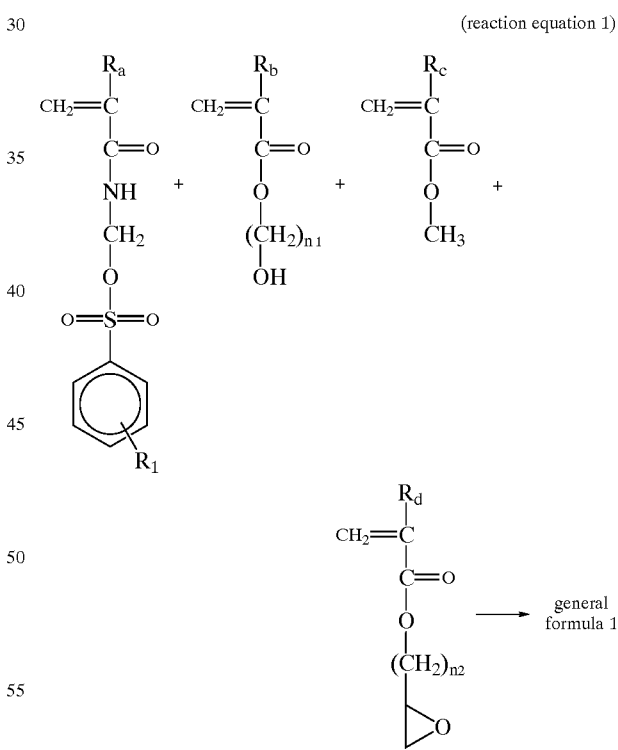

wherein, $R_a$, $R_b$, $R_c$ and $R_d$ each represents hydrogen or methyl; $R_1$ represents hydrogen, hydroxy, a substituted or non-substituted straight or branched $C_1$–$C_5$ alkyl, cycloalkyl, alkoxyalkyl or cycloalkoxyalkyl; and $n_1$ and $n_2$ each represents an integer of 1 to 4.

The polymers represented by general formula 2 above can be prepared in accordance with the reaction equation 2 set forth below, wherein a p-tosylalkylacrylamide-type monomer, an hydroxyalkylacrylate-type monomer and a methylacrylate-type monomer are polymerized with the aid of an initiator in a solvent. Each of the monomers has a mole fraction ranging from 0.01 to 0.99.

(reaction equation 2)

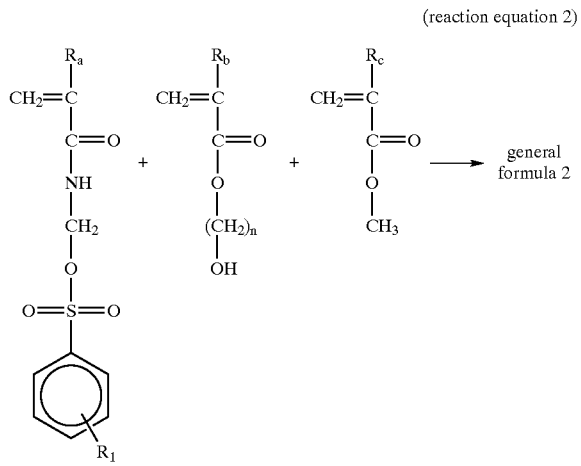

wherein, $R_a$, $R_b$, and $R_c$ each represents hydrogen or methyl; $R_1$ represents hydrogen, hydroxy, a substituted or non-substituted straight or branched $C_1$–$C_5$ alkyl, cycloalkyl, alkoxyalkyl or cycloalkoxyalkyl; and n represents an integer of 1 to 4.

Conventional radical initiators, preferably 2,2-azobisisobutyronitrile (AIBN), acetylperoxide, laurylperoxide or t-butylperoxide, may be used for initiating the polymerization reaction forming the polymers of general formulas 1 and 2. Also, conventional solvents may be used for the polymerization, preferably tetrahydrofuran, toluene, benzene, methylethylketone or dioxane. Preferably, the polymerization for the polymers of the general formulas 1 and 2 is carried out at 50–80° C.

Semiconductor devices of the present invention may be prepared as described below. The copolymer of general formula 1 or formula 2 may be dissolved in a suitable solvent alone, or with a cross-linker additive selected from acrolein, diethylacetal and melamine-type cross linkers, at an amount of 0.1 to 30 % by weight. The solution is filtered and coated on a wafer and then hard-baked to form a cross-linked anti-reflective coating. Semiconductor devices can then be fabricated therefrom in the conventional manner.

Conventionl organic solvents may be used in preparing the anti-reflective coating composition, with preference given to ethyl 3-ethoxypropionate, methyl 3-methoxy propionate, cyclohexanone or propyleneglycol methylether-acetate. The solvent is preferably used at an amount of 200 to 5000% by weight based on the weight of the anti-reflective coating resin copolymer used.

It has been found that the anti-reflective coatings of the present invention exhibit high performance in photolithography processes for forming ultrafine-patterns using 193 nm ArF radiation. The same was also true of where 248 nm KrF, 157 nm $F_2$ laser, E-beams, EUV (extremely ultraviolet) and ion beams are used as light sources.

The following examples are set forth to illustrate more clearly the principles and practice of this invention to one skilled in the art. As such, they are not intended to limit the invention, but are illustrative of certain preferred embodiments.

EXAMPLE 1

Synthesis of p-Tosylmethylacrylamide Monomer

After 48% (w/w) of N-hydroxymethylacrylamide monomer dissolved in water is added to diethylether or normal hexane, the solution is precipitated, separated and dried. 30.33 g (0.3 mole) of N-hydroxymethylacrylamide and 66.73 g (0.35 mole) of p-toluene sulfonylchloride are each respectively added to 40.48 g (0.4 mole) of triethylamine and the mixtures are dissolved completely. In a 500 ml round-bottom flask in a nitrogen atmosphere, the N-hydroxymethylacrylamide/triethylamine mixture is reacted with the p-toluenesulfonylchloride/triethylamine mixture, which is slowly added thereto with stirring. The reaction is continued for more than 24 hours. While the reaction is being conducted, the rate of reaction is checked by TLC. After the completion of reaction, the mixture is neutralized with sulfuric acid and washed with deionized water. The reactant in the organic solvent layer is extracted, the water in the organic solvent is removed with $MgSO_4$ and the residue is distilled under the reduced pressure, to produce the monomer represented by the following chemical formula 1. The yield is 85–90%.

(chemical formula 1)

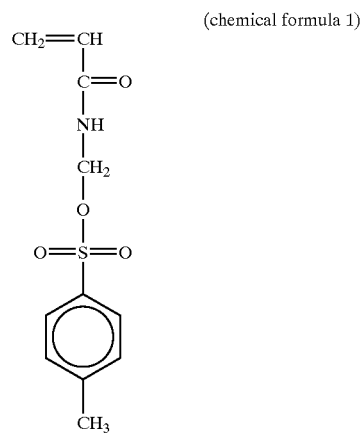

EXAMPLE 2

Synthesis of p-Tosylmethylmethacrlamide Monomer

After 52.6% (w/w) of N-hydroxymethylmethacrylamide monomer dissolved in water is added to diethylether or normal hexane, the solution is precipitated, separated and dried. The 34.54 g (0.3 mole) of N-hydroxymethylmethacrylamide and 66.73 g (0.35 mole) of p-toluene sulfonylchloride are each respectively added to 40.48 g (0.4 mole) of triethylamine and the mixtures are dissolved completely. Thereafter, in a 500 ml round-bottom flask, the N-hydroxymethylmethacrylamide/triethylamine is reacted with the p-toluenesulfonylchloride/triethylamine, which is slowly added thereto with stirring in a nitrogen atmosphere. The reaction is continued for more than 24 hours. While the reaction is continued, the rate of reaction is checked by TLC. After the completion of reaction, the mixture is neutralized with sulfuric acid and washed with deionized water. And the reactant in the organic solvent layer is extracted, the water in the organic solvent is removed with $MgSO_4$ and the residue is distilled under the reduced pressure, to produce the monomer represented by the following chemical formula 2. The yield is 85–90%.

(chemical formula 2)

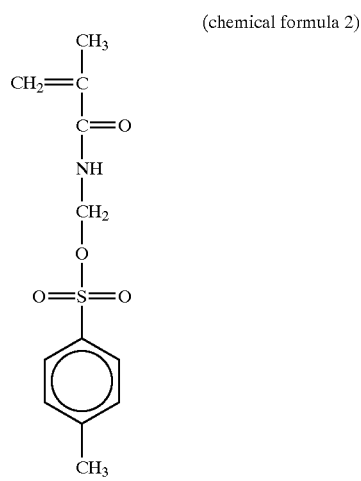

EXAMPLE 3

Synthesis of the Copolymer Poly
(tosylmethylacrylamide-hydroxyethylacrylate-
methylmethacrylate-glycidylmethacrylate)

In a 500 ml round-bottom flask are placed 71.78 g (0.3 mole) of p-tosylmethylacrylamide, 29 g (0.25 mole) of hydroxyethylacrylate, 10.01 g (0.1 mole) of methylmethacrylate, and 42.65 g (0.3 mole) of glycidylmethacrylate. This mixture is added to 300 g of separately prepared tetrahydrofuran (THF) with stirring and mixed completely. Thereafter, in the presence of 0.1 g–3 g of 2, 2' azobisisobutyronitrile (AIBN), the reaction is subjected to polymerization at 60–75° C. for 5–20 hours in a nitrogen atmosphere. After completion of polymerization, the solution is precipitated in ethyl ether or normal hexane and the precipitate is filtered and dried to produce poly(tosylmethylacrylamide-hydroxyethylacrylate-methylmethacrylate-glycidylmethacrylate), represented by chemical formula 3. The yield is 70–75%.

(chemical formula 3)

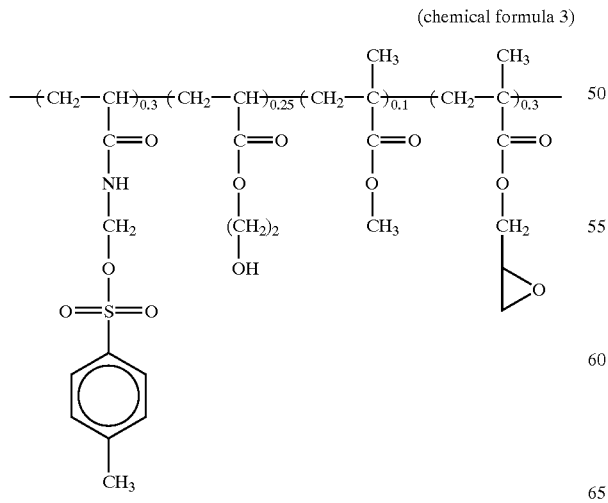

EXAMPLE 4

Synthesis of the Copolymer Poly
(tosylmethylacrylamide Hydroxyethylmethacrylate-
methylmethacylate-glycidylmethacrylate)

In a 500 ml round-bottom flask are placed 78.96 g (0.33 mole) of p-tosylmethylacrylamide, 26 g (0.2 mole) of hydroxyethylmethacrylate, 15.17 g (0.15 mole) of methylmethacrylate and 42.65 g (0.3 mole) of glycidylmethacrylate. This mixture is added to 300 g of separately prepared tetrahydrofuran(THF) with stirring and mixed completely. Thereafter, in the presence of 0.1–3 g of AIBN, the reaction is subjected to polymerization at 60–75° C. for 5–20 hours in a nitrogen atmosphere. After completion of the polymerization, the solution was precipitated in ethyl ether or normal hexane and the precipitate is filtered and dried to produce poly(tosylmethylacrylamide-hydroxyethylmethacrylate-methylmethacrylate-glycidylmethacrylate), represented by chemical formula 4. The yield is 70–75%

(chemical formula 4)

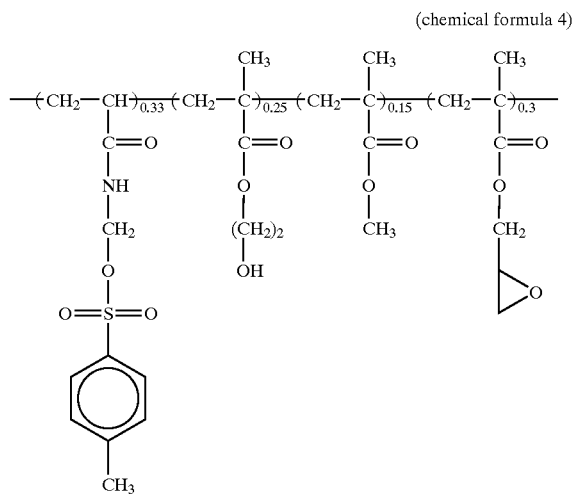

EXAMPLE 5

Synthesis of the Copolymer Poly
(tosylmethylacrylamide Hydroxypropylacrylate-
methylmethacylate-glycidylmethacrylate)

In a 500 ml round-bottom flask are placed 71.78 g (0.3 mole) of p-tosylmethylacrylamide, 32.54 g (0.25 mole) of hydroxypropylacrylate, 10.01 g (0.1 mole) of methylmethacrylate and 42.65 g (0.3 mole) of glycidylmethacrylate. This mixture is added to 300 g of separately prepared tetrahydrofuran(THF) with stirring and mixed completely. Thereafter, in the presence of 0.1–3 g of AIBN, the reaction is subjected to polymerization at 60–75° C. for 5–20 hours in a nitrogen atmosphere. After completion of the polymerization, the solution is precipitated in ethyl ether or normal hexane and the precipitate is filtered and dried to produce poly(tosylmethylacrylamide-hydroxypropylacrylate-methylmethacrylate-glycidylmethacrylate) represented by chemical formula 5. The yield is 70–75%.

(chemical formula 5)

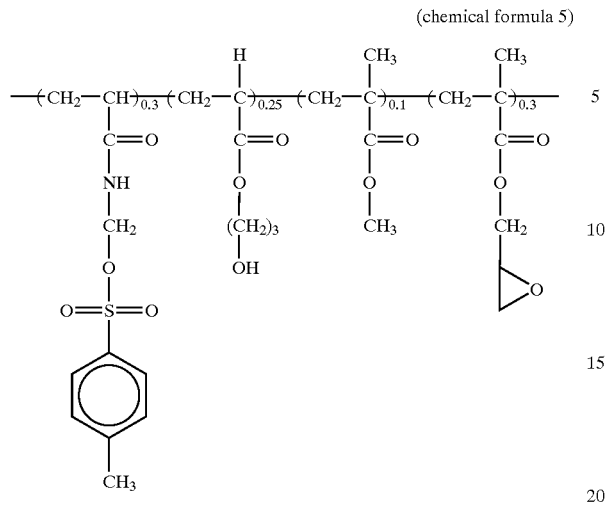

EXAMPLE 6

Synthesis of the Copolymer Poly (tosylmethylacrylamide Hydroxypropylmethacrylate-methylmethacylate-glycidylmethacrylate)

In a 500 ml round-bottom flask are placed 71.78 g (0.33 mole) of p-tosylmethylacrylamide, 33.14 g (0.23 mole) of hydroxypropylmethacrylate, 10.01 g (0.1 mole) of methylmethacrylate and 42.65 g (0.3 mole) of glycidylmethacrylate. This mixture is added to 300 g of separately prepared tetrahydrofuran(THF) with stirring and mixed completely. Thereafter, in the presence of 0.1–3 g of AIBN, the reaction is subjected to polymerization at 60–75° C. for 5–20 hours in a nitrogen atmosphere. After completion of the polymerization, the solution is precipitated in ethyl ether or normal hexane and the precipitate is filtered and dried to produce poly (tosylmethylacrylamide-hydroxypropylmethacrylate-methylmethacrylate-glycidylmethacrylate), represented by chemical formula 6. The yield is 70–75%.

(chemical formula 6)

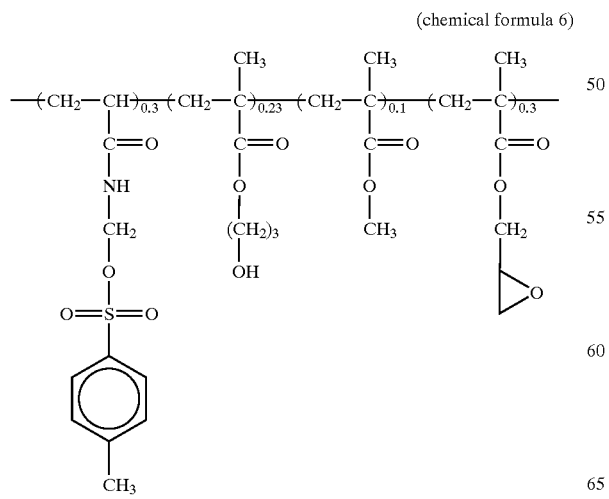

EXAMPLE 7

Synthesis of the Copolymer Poly (tosylmethylacrylamide-hydroxybutylacrylate-methylmethacylate-glycidylmethacrylate)

In a 500 ml round-bottom flask are placed 71.78g (0.3 mole) of p-tosylmethylacrylamide, 28.83 g (0.2 mole) of hydroxybutylacrylate, 10.01 g (0.1 mole) of methylmethacrylate and 42.65 g (0.3 mole) of glycidylmethacrylate. This mixture is added to 300 g of separately prepared tetrahydrofuran(THF) with stirring and mixed completely. Thereafter, in the presence of 0.1–3 g of AIBN, the reaction is subjected to polymerization at 60–75° C. for 5–20 hours in a nitrogen atmosphere. After completion of the polymerization, the solution is precipitated in ethyl ether or normal hexane and the precipitate is filtered and dried to produce poly(tosylmethylacrylamide-hydroxybutylacrylate-methylmethacrylate-glycidylmethacrylate), represented by chemical formula 7. The yield is 65–70%.

(chemical formula 7)

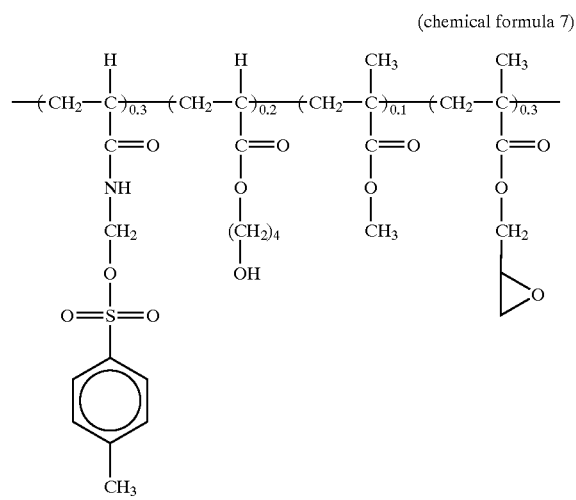

EXAMPLE 8

Synthesis of the Copolymer Poly (tosylmethylmethacrylamide-hydroxyethylmetacrylate-methylacrylate-glycidylmethacrylate)

In a 500 ml round-bottom flask are placed 75.99 g (0.3 mole) of p-tosylmethylmethacrylamide, 29.03 g (0.25 mole) of hydroxyethylmethacrylate, 15.02 g (0.15 mole) of methylacrylate and 42.65 g (0.3 mole) of glycidylmethacrylate. This mixture was added to 300 g of separately prepared tetrahydrofuran(THF) with stirring and mixed completely. Thereafter, in the presence of 0.1–3 g of AIBN, the reaction is subjected to polymerization at 60–75° C. for 5–20 hours in a nitrogen atmosphere. After completion of the polymerization, the solution is precipitated in ethyl ether or normal hexane and the precipitate is filtered and dried to produce poly (tosylmethylmethacrylamide-hydroxyethylmethacrylate-methylacrylateglycidylmethacrylate), represented by chemical formula 8. The yield is 70–75%.

(chemical formula 8)

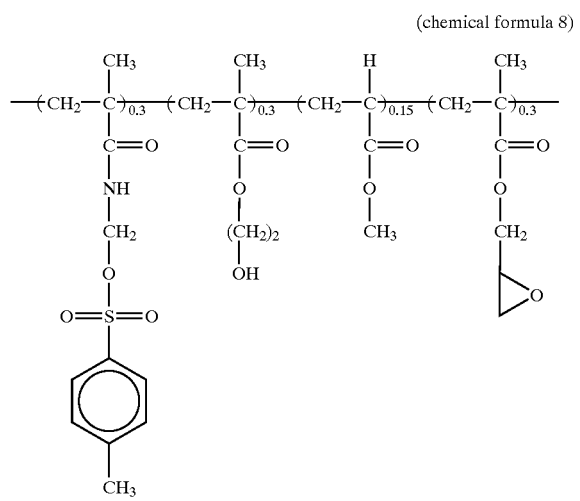

EXAMPLE 9

Synthesis of the Copolymer Poly (tosylmethylmethacrylamide-hydroxyethylacrylate-methylmethacylate-glycidylmethacrylate)

In a 500 ml round-bottom flask are placed 75.99 g (0.3 mole) of p-tosylmethylmethacrylamide, 26.3 g (0.2 mole) of hydroxyethylacrylate, 12.91 g (0.1 5 mole) of methylmethacrylate and 42.65 g (0.3 mole) of glycidylmethacrylate. This mixture is added to 300 g of separately prepared tetrahydrofuran (THF) with stirring and mixed completely. Thereafter, in the presence of 0.1–3 g of AIBN, the reaction is subjected to polymerization at 60–75° C. for 5–20 hours in a nitrogen atmosphere. After completion of the polymerization, the solution is precipitated in ethyl ether or normal hexane and the precipitate is filtered and dried to produce poly(tosylmethylmethacrylamide-hydroxyethylacrylate-methylmethacrylate-glycidylmethacrylate), represented by chemical formula 9. The yield is 70–75%.

(chemical formula 9)

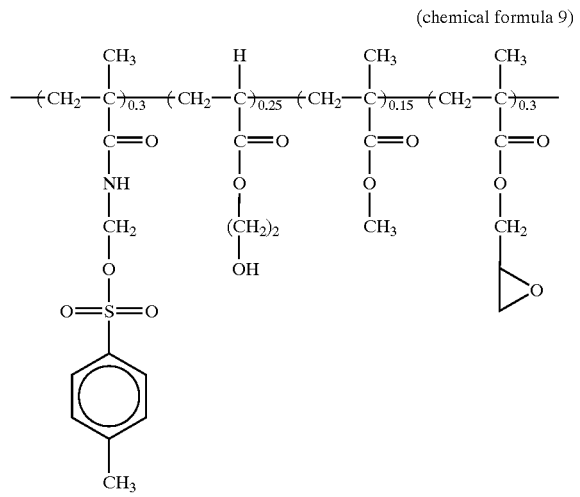

EXAMPLE 10

Synthesis of the Copolymer Poly (tosylmethylmethacrylamide-hydroxypropylmethacrylate-methylmethacylate-glycidylmethacrylate)

In a 500 ml round-bottom flask are placed 75.99 g (0.3 mole) of p-tosylmethylmethacrylamide, 32.54 g (0.25 mole) of hydroxypropylmethacrylate, 15.02 g (0.15 mole) of methylmethacrylate and 42.65 g (0.3 mole) of glycidylmethacrylate. This mixture was added to 300 g of separately prepared tetrahydrofuran (THF) with stirring and mixed completely. Thereafter, in the presence of 0.1–3 g of AIBN, the reaction is subjected to polymerization at 60–75° C. for 5–20 hours in a nitrogen atmosphere. After completion of the polymerization, the solution is precipitated in ethylether or normal hexane and the precipitate is filtered and dried to produce poly (tosylmethylmethacrylamide-hydroxypropylmethacrylate-methylmethacrylate-glycidylmethacrylate), represented by chemical formula 10. The yield is 70–75%.

(chemical formula 10)

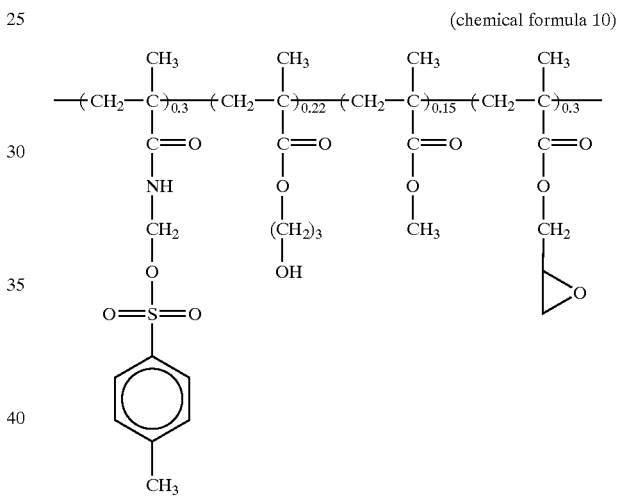

EXAMPLE 11

Synthesis of the Copolymer Poly (tosylmethylmethacrylamide-hydroxypropylmethacrylate-methylacrylate-glycidylmethacrylate)

In a 500 ml round-bottom flask are placed 75.99 g (0.3 mole) of p-tosylmethylmethacrylamide, 31.72 g (0.22 mole) of hydroxypropylmethacrylate, 12.91 g (0.15 mole) of methylacrylate and 42.65 g (0.3 mole) of glycidylmethacrylate. This mixture is added to 300 g of separately prepared tetrahydrofuran (THF) with stirring and mixed completely. Thereafter, in the presence of 0.1–3 g of AIBN, the reaction is subjected to polymerization at 60–75° C. for 5–20 hours in a nitrogen atmosphere. After completion of the polymerization, the solution is precipitated in ethyl ether or normal hexane and the precipitate is filtered and dried to produce poly (tosylmethylmethacrylamide-hydroxypropylmethacrylate-methylacrylate-glycidylmethacrylate), represented by chemical formula 11.

The yield is 65–70%.

(chemical formula 11)

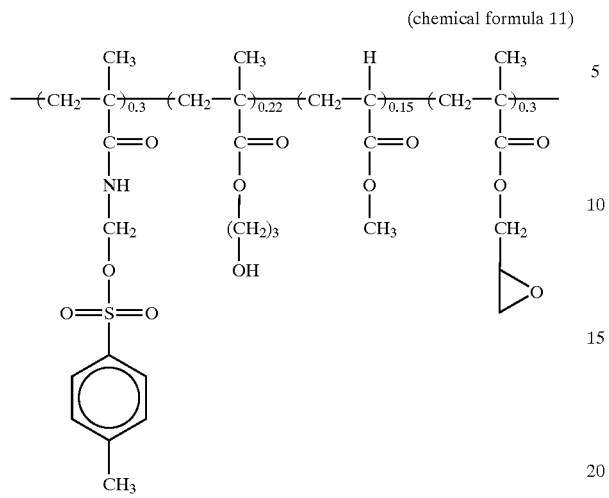

EXAMPLE 12

Synthesis of the Copolymer Poly
(tosylmethylmethacrylamide-hydroxybutylacrylate-
methylmethacylate-glycidylmethacrylate)

In a 500 ml round-bottom flask are placed 75.99 g (0.3 mole) of p-tosylmethylmethacrylamide, 28.83 g (0.2 mole) of hydroxybutylacrylate, 10.01 g (0.15 mole) of methylmethacrylate and 42.65 g (0.3 mole) of glycidylmethacrylate. This mixture was added to 300 g of separately prepared tetrahydrofuran (THF) with stirring and mixed completely. Thereafter, in the presence of 0.1–3 g of AIBN, the reaction is subjected to polymerization at 60–75° C. for 5–20 hours in a nitrogen atmosphere. After completion of the polymerization, the solution is precipitated in ethyl ether or normal hexane and the precipitate is filtered and dried to produce poly (tosylmethylmethacrylamide-hydroxybutylacrylate-methylmethacrylate-glycidylmethacrylate), represented by chemical formula 12. The yield is 65–70%.

(chemical formula 12)

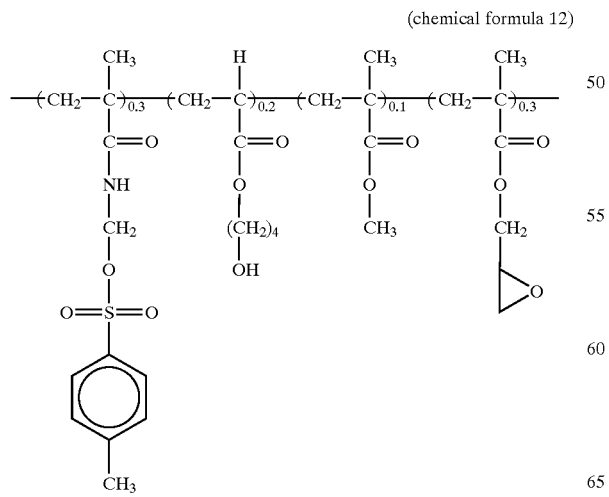

EXAMPLE 13

Synthesis of the Copolymer Poly
(tosylmethylacrylamide-hydroxyethylacrylate-
methylmethacylate)

In a 500 ml round-bottom flask are placed 71.78 g (0.3 mole) of p-tosylmethylacrylamide, 34.84 g (0.3 mole) of hydroxyethylacrylate and 25.03 g (0.25 mole) of methylmethacrylate. This mixture is added to 300 g of separately prepared tetrahydrofuran (THF) with stirring and mixed completely. Thereafter, in the presence of 0.1–3 g of AIBN, the reaction is subjected to polymerization at 60–75° C. for 5–20 hours in a nitrogen atmosphere. After completion of the polymerization, the solution is precipitated in ethyl ether or normal hexane and the precipitate is filtered and dried to produce poly(tosylmethylacrylamide-hydroxyethylacrylate-methylmethacrylate), represented by chemical formula 13. The yield is 70–75%.

(chemical formula 13)

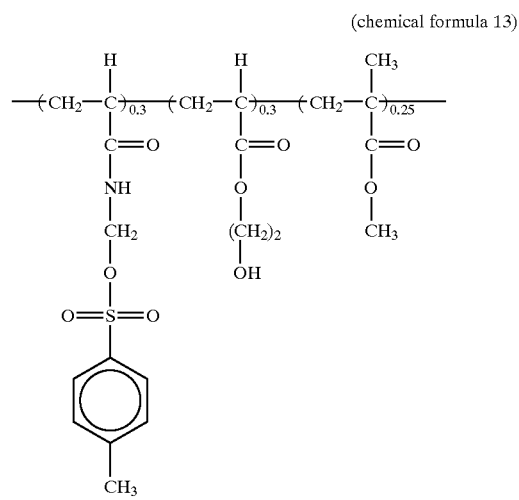

EXAMPLE 14

Synthesis of the Copolymer Poly
(tosylmethylacrylamide-hydroxyethylmethacrylate-
methylmethacylate).

In a 500 ml round-bottom flask are placed 78.96 g (0.33 mole) of p-tosylmethylacrylamide, 45.55 g (0.35 mole) ofhydroxyethylmethacrylate and 25.03 g (0.25 mole) of methylmethacrylate. This mixture is added to 300 g of separately prepared tetrahydrofuran(THF) with stirring and mixed completely. Thereafter, in the presence of 0.1–3 g of AIBN, the reaction is subjected to polymerization at 60–75° C. for 5–20 hours in a nitrogen atmosphere. After completion of the polymerization, the solution is precipitated in ethyl ether or normal hexane and the precipitate is filtered and dried to produce poly(tosylmethylacrylamide-hydroxyethylmethacrylate-methylmethacrylate), represented by chemical formula 14. The yield is 70–75%.

(chemical formula 14)

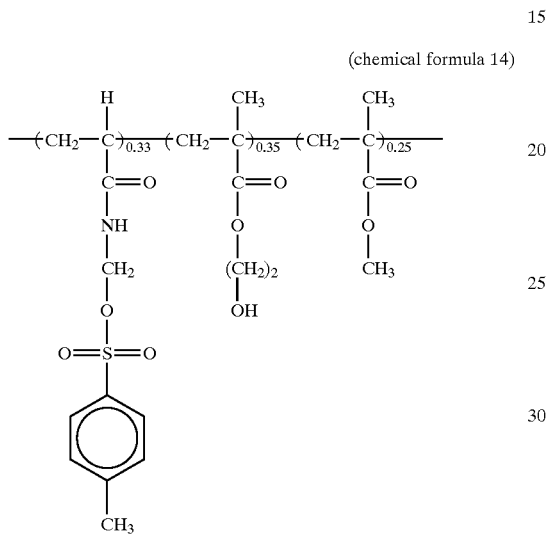

EXAMPLE 15

Synthesis of the Copolymer Poly(tosylmethylacrylamide-hydroxypropylacrylate-methylmethacylate)

In a 500 ml round-bottom flask are placed 71.78 g (0.3 mole) of p-tosylmethylacrylamide, 42.95 g (0.33 mole) of hydroxypropylacrylate and 22.03 g (0.22 mole) of methylmethacrylate. This mixture is added to 300 g of separately prepared tetrahydrofuran(THF) with stirring and mixed completely. Thereafter, in the presence of 0.1–3 g of AIBN, the reaction is subjected to polymerization at 60–75° C. for 5–20 hours in a nitrogen atmosphere. After completion of the polymerization, the solution is precipitated in ethyl ether or normal hexane and the precipitate is filtered and dried to produce poly(tosylmethylacrylamide-hydroxypropylacrylate-methylmethacrylate) represented by chemical formula 15. The yield is 70–75%.

(chemical formula 15)

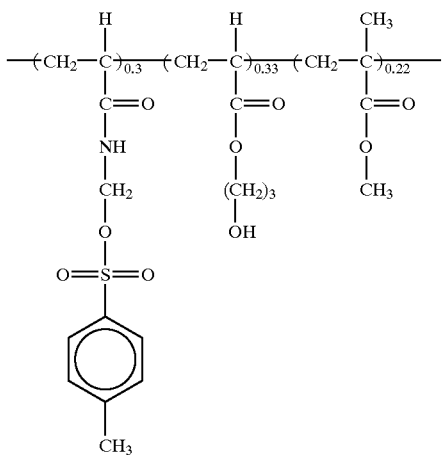

EXAMPLE 16

Synthesis of the Copolymer Poly(tosylmethylacrylamide-hydroxypropylmethacrylate-methylmethacylate)

In a 500 ml round-bottom flask are placed 71.78 g (0.3 mole) of p-tosylmethylacrylamide, 47.58 g (0.33 mole) of hydroxypropylmethacrylate and 25.03 g (0.25 mole) of methylmethacrylate. This mixture is added to 300 g of separately prepared tetrahydrofuran (THF) with stirring and mixed completely. Thereafter, in the presence of 0.1–3 g of AIBN, the reaction is subjected to polymerization at 60–75° C. for 5–20 hours in a nitrogen atmosphere. After completion of the polymerization, the solution is precipitated in ethyl ether or normal hexane and the precipitate is filtered and dried to produce a poly(tosylmethylacrylamide-hydroxypropylmethacrylate-methylmethacrylate), represented by chemical formula 16. The yield is 70–75%.

(chemical formula 16)

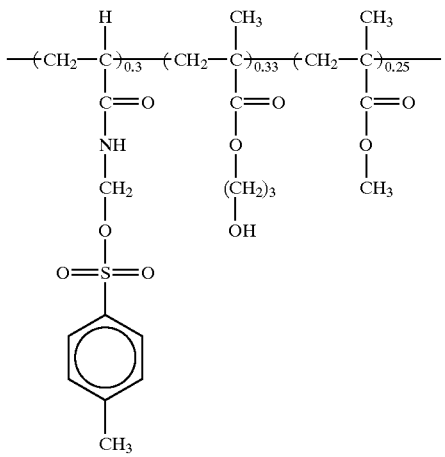

EXAMPLE 17

Synthesis of the Copolymer Poly(tosylmethylacrlyamide-hydroxybutylacrylate-methylmethacylate)

In a 500 ml round-bottom flask are placed 71.78 g (0.3 mole) of p-tosylmethylacrylamide, 43.25 g (0.3 mole) of hydroxybutylacrylate and 25.03 g (0.3 mole) of methylmethacrylate. This mixture is added to 300 g of separately prepared tetrahydrofuran (THF) with stirring and mixed completely. Thereafter, in the presence of 0.1–3 g of AIBN, the reaction is subjected to polymerization at 60–75° C. for 5–20 hours in a nitrogen atmosphere. After completion of the polymerization, the solution is precipitated in ethyl ether or normal hexane and the precipitate is filtered and dried to produce poly(tosylmethylacrylamide-hydroxybutylacrylate-methylmethacrylate) represented by chemical formula 17. The yield is 70–75%.

(chemical formula 17)

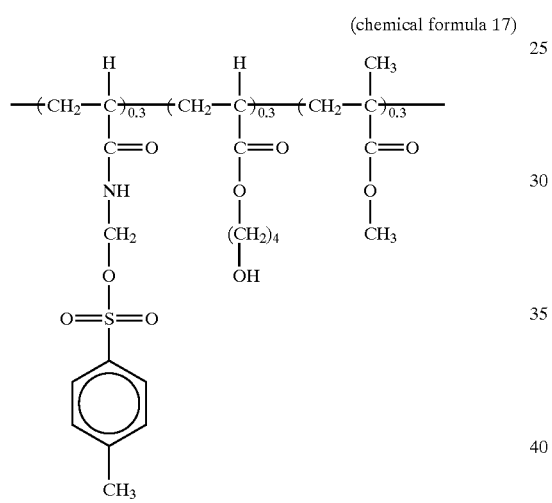

EXAMPLE 18

Synthesis of the Copolymer Poly(tosylmethylmethacrylamide-hydroxyethylacrylate-methylmethacylate)

In a 500 ml round-bottom flask are placed 75.99 g (0.3 mole) of p-tosylmethylmethacrylamide, 29.03 g (0.25 mole) of hydroxyethylacrylate and 29.03 g (0.25 mole) of methylmethacrylate. This mixture is added to 300 g of separately prepared tetrahydrofuran (THF) with stirring and mixed completely. Thereafter, in the presence of 0.1–3 g of AIBN, the reaction is subjected to polymerization at 60–75° C. for 5–20 hours in a nitrogen atmosphere. After completion of the polymerization, the solution is precipitated in ethyl ether or normal hexane and the precipitate is filtered and dried to produce poly(tosylmethylmethacrylamide-hydroxyethylacrylate-methylmethacrylate), represented by chemical formula 18. The yield is 70–7 5%.

(chemical formula 18)

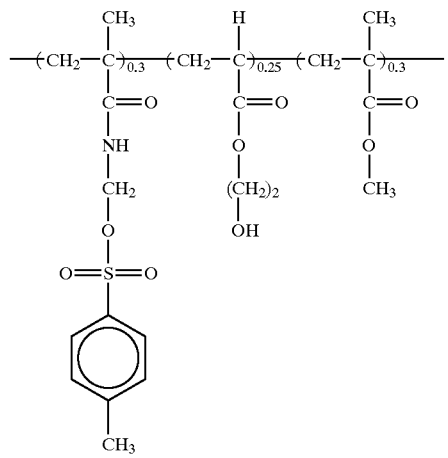

EXAMPLE 19

Synthesis of the Copolymer Poly(tosylmethylmethacrylamide-hydroxyethylmethacrylate-methylmethacylate)

In a 500 ml round-bottom flask are placed 75.99 g (0.3 mole) of p-tosylmethylmethacrylamide, 41.64 g (0.32 mole) of hydroxyethylmethacrylate and 25.03 g (0.3 mole) of methylmethacrylate. This mixture is added to 300 g of separately prepared tetrahydrofuran (THF) with stirring and mixed completely. Thereafter, in the presence of 0.1–3 g of AIBN, the reaction is subjected to polymerization at 60–75° C. for 5–20 hours in a nitrogen atmosphere. After completion of the polymerization, the solution is precipitated in ethyl ether or normal hexane and the precipitate is filtered and dried to produce poly(tosylmethylmethacrylamide-hydroxyethylmethacrylate-methylmethacrylate), represented by chemical formula 19. The yield is 70–75%.

(chemical formula 19)

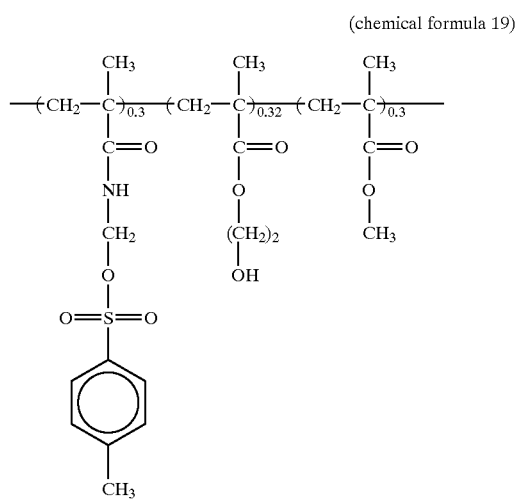

EXAMPLE 20

Synthesis of the Copolymer Poly(tosylmethylmethacrylamide-hydroxypropylacrylate-methylmethacylate)

In a 500 ml round-bottom flask are placed 75.99 g (0.3 mole) of p-tosylmethylmethacrylamide, 42.95 g (0.33 mole)

of hydroxypropylacrylate and 25.03 g (0.3 mole) of methylmethacrylate. This mixture is added to 300 g of separately prepared tetrahydrofuran (THF) with stirring and mixed completely. Thereafter, in the presence of 0.1–3 g of AIBN, the reaction is subjected to polymerization at 60–75° C. for 5–20 hours in a nitrogen atmosphere. After completion of the polymerization, the solution is precipitated in ethyl ether or normal hexane and the precipitate is filtered and dried to produce poly(tosylmethylmethacrylamide-hydroxypropylacrylate-methylmethacrylate) represented by chemical formula 20. The yield is 70–75%.

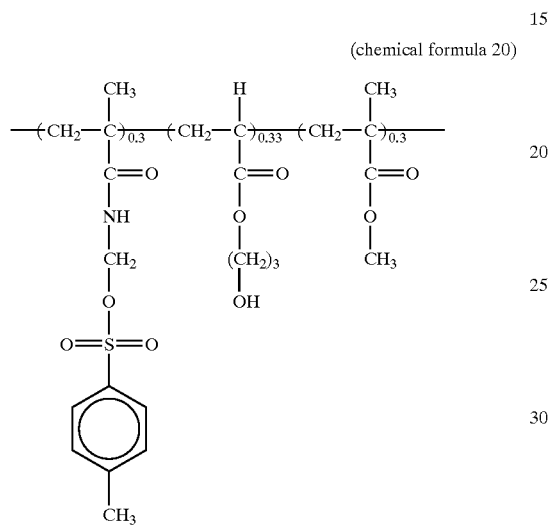

(chemical formula 20)

EXAMPLE 21

Synthesis of the Copolymer Poly(tosylmethylmethacrylamide-hydroxypropylmethacrylate-methylmethacylate)

In a 500 ml round-bottom flask are placed 75.99 g (0.3 mole) of p-tosylmethylmethacrylamide, 43.25 g (0.3 mole) of hydroxypropylmethacrylate and 25.03 g (0.3 mole) of methylmethacrylate. This mixture is added to 300 g of separately prepared tetrahydrofuran (THF) with stirring and mixed completely. Thereafter, in the presence of 0. 1–3 g of AIBN, the reaction is subjected to polymerization at 60–75° C. for 5–20 hours in a nitrogen atmosphere. After completion of the polymerization, the solution is precipitated in ethyl ether or normal hexane and the precipitate is filtered and dried to produce poly(tosylmethylmethacrylamide-hydroxypropylmethacrylate-methylmethacrylate), represented by chemical formula 21. The yield is 70–75%.

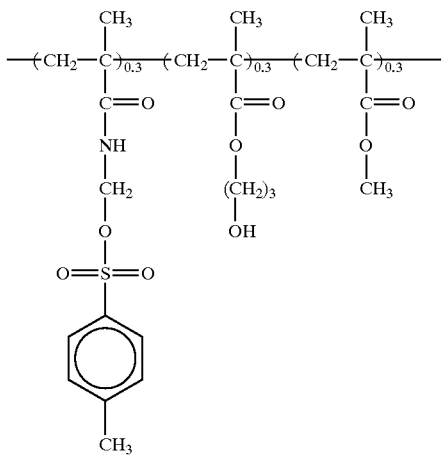

(chemical formula 21)

EXAMPLE 22

Synthesis of the Copolymer Poly(tosylmethylmethacrylamide-hydroxybutylacrylate-methylmethacylate)

In a 500 ml round-bottom flask are placed 75.99 g (0.3 mole) of p-tosylmethylmethacrylamide, 47.58 g (0.33 mole) of hydroxybutylacrylate and 25.03 g (0.3 mole) of methylmethacrylate. This mixture is added to 300 g of separately prepared tetrahydrofuran (THF) with stirring and mixed completely. Thereafter, in the presence of 0.1–3 g of AIBN, the reaction is subjected to polymerization at 60–75° C. for 5–20 hours in a nitrogen atmosphere. After completion of the polymerization, the solution is precipitated in ethyl ether or normal hexane and the precipitate is filtered and dried to produce poly(tosylmethylmethacrylamide-hydroxybuthylacrylate-methylmethacrylate) represented by chemical formula 22. The yield is 65–70%.

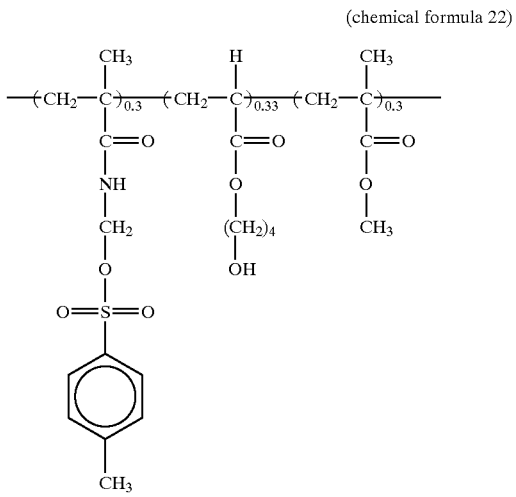

(chemical formula 22)

EXAMPLE 23

Preparation of Anti-reflective Coating Film

A resin having the chemical structure of general formula 1, obtained in each of Examples 5 to 12, is dissolved in 200–5,000% (w/w) of propyleneglycolmethyletheracetate (PGMEA). This solution is filtered, coated on a wafer, and hard-baked at 100–300° C. for 10–1,000 seconds. Afterwards, a photoresist film is coated over the anti-reflective coating thus formed and imaged to form ultrafine patterns.

EXAMPLE 24

Preparation of Anti-reflective Coating Film

A resin having a chemical structure of general formula 2, obtained in each of Examples 13 to 22 is dissolved in 200–5,000% (w/w) of propyleneglycolmethyletheracetate (PGMEA). This solution, alone or in combination with 0.1–30% by weight of at least one cross-linker selected from acrolein dimethylacetal, acrolein diethylacetal and melamine-type cross-linkers is filtered, coated on a wafer, and hard-baked at 100–300° C. for 10–1,000 seconds. Afterwards, a photoresist film is coated on the anti-reflective coating thus formed and imaged to form ultrafine patterns.

As described hereinbefore, the anti-reflective coating polymers of general formula 1 or 2, for example, the copolymer resins of chemical formulas 3 to 22, contain phenyl and amide linkage showing superior radiation absorbency at 193 nm wavelength, and are thereby suitable for anti-reflective coatings. When the polymers of the present invention are used as anti-reflective coatings in the ultrafine-pattern formation process of preparing semiconductors, the product yield is increased because CD variation originating from lower layers is eliminated and stable 64 M, 256 M, 1 G, 4 G, 16 G DRAM ultrafine-patterns are formed.

What is claimed is:

1. A polymer represented by the general formula 1:

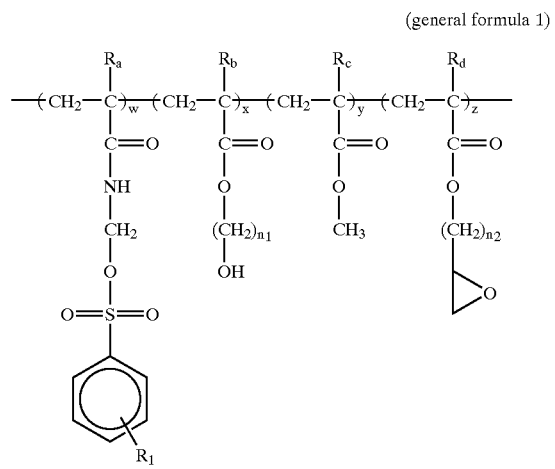

(general formula 1)

wherein, $R_a$, $R_b$, $R_c$ and $R_d$ each represents hydrogen or methyl; $R_1$ represents hydrogen, hydroxy, a substituted or non-substituted straight or branched $C_1$–$C_5$ alkyl, cycloalkyl, alkoxyalkyl or cycloalkoxyalkyl; w, x, y and z each represents mole fraction of 0.01–0.99; and $n_1$ and $n_2$ each represents an integer of 1 to 4.

2. A polymer according to the claim 1 wherein $R_1$ represents methyl.

3. A polymer according to the claim 1 wherein the polymer is poly (tosylmethylacrylamide-hydroxyethylacrylate-methylmethacrylate-glycidylmethacrylate) and the ratio of w:x:y:z is 0.3:0.25:0.1:0.3.

4. A polymer according to the claim 1, wherein the polymer is poly (tosylmethylacrylamide-hydroxyethylmethacrylate-methylmethacrylate-glycidylmethacrylate) and the ratio of w:x:y:z is 0.3:0.2:0.1:0.3.

5. A polymer according to the claim 1, wherein the polymer is poly (tosylmethylacrylamide-hydroxypropylacrylate-methylmethacrylate-glycidylmethacrylate) and the ratio of w:x:y:z is 0.3:0.25:0.1:0.3.

6. A polymer according to the claim 1, wherein the polymer is poly (tosylmethylacrylamide-hydroxypropylmethacrylate-methylmethacrylate-glycidylmethacrylate) and the ratio of w:x:y:z is 0.3:0.23:0.1:0.3.

7. A polymer according to the claim 1, wherein the polymer is poly (tosylmethylacrylamide-hydroxybutylacrylate-methylmethacrylate-glycidylmethacrylate) and the ratio of w:x:y:z is 0.3:0.2:0.1:0.3.

8. A polymer according to the claims wherein the polymer is poly (tosylmethylmethacrylamide-hydroxyethylmethacrylate-methylacrylate-glycidylmethacrylate) and the ratio of w:x:y:z is 0.3:0.25:0.15:0.3.

9. A polymer according to the claim 1, wherein the polymer is poly (tosylmethylmethacrylamide-hydroxyethylacrylate-methylmethacrylate-glycidylmethacrylate) and the ratio of w:x:y:z is 0.3:0.2:0.15:0.3.

10. A polymer according to the claim 1, wherein the polymer is poly (tosylmethylmethacrylamide-hydroxypropylmethacrylate-methylmethacrylate-glycidylmethacrylate) and the ratio of w:x:y:z is 0.3:0.25:0.15:0.3.

11. A polymer according to the claim 1, wherein the polymer is poly (tosylmethylmethacrylamide-hydroxypropylmethacrylate-methylacrylate-glycidylmethacrylate) and the ratio of w:x:y:z is 0.3:0.22:0.15:0.3.

12. A polymer according to the claim 1, wherein the polymer is poly (tosylmethylmethacrylamide-hydroxybutylacrylate-methylmethacrylate-glycidylmethacrylate) and the ratio of w:x:y:z is 0.3:0.2:0.1:0.3.

13. A method for preparing a polymer of claim 1 which comprises polymerizing a tosylalkylacrylamide-type monomer, a hydroxyalkylacrylate-type monomer, an alkylacrylate-type monomer and a glycidylmethacrylate-type monomer in a solvent in the presence of an initiator as shown in the following reaction equation 1:

(reaction equation 1)

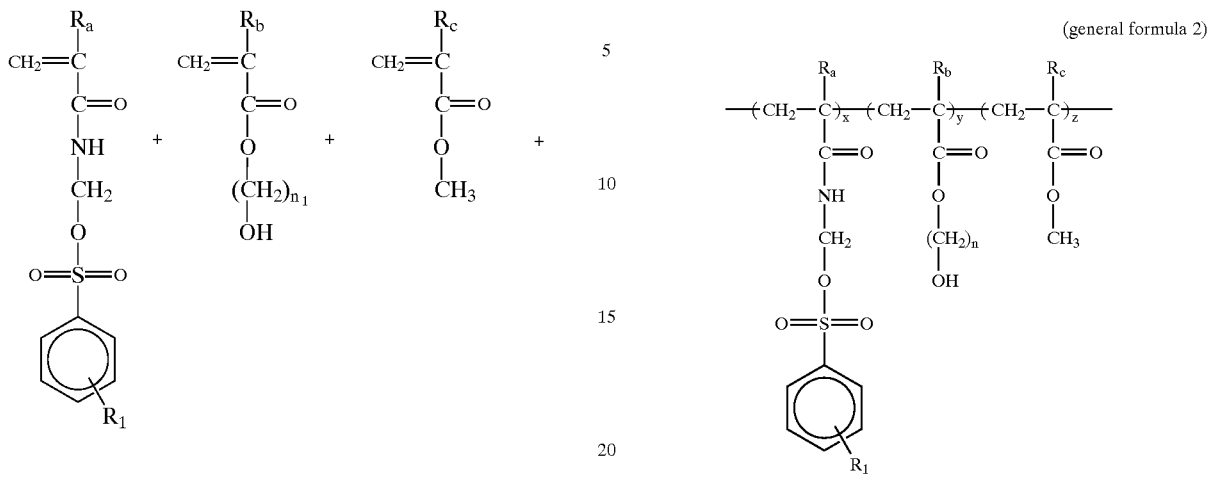

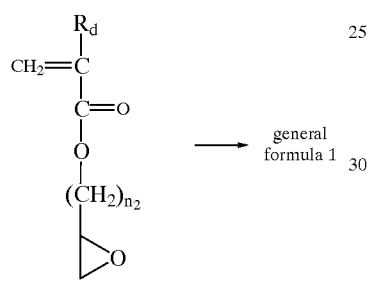

→ general formula 1 wherein, $R_a$, $R_b$, $R_c$ and $R_d$ each represents hydrogen or methyl; $R_1$ represents hydrogen, hydroxy, a substituted or non-substituted straight or branched $C_1$–$C_5$ alkyl, cycloalkyl, alkoxyalkyl or cycloalkoxyalkyl; and $n_1$ and $n_2$ each represents an integer of 1 to 4.

14. A method according to the claim 13, wherein $R_1$ represents methyl and the mole fraction of each monomer is 0.01–0.99.

15. A method according to the claim 13, wherein the initiator is selected from the group consisting of 2,2-azobisisobutyronitrile(AIBN), acetylperoxide, laurylperoxide and t-butylperoxide.

16. A method according to the claim 13, wherein the solvent is selected from the group consisting of tetrahydrofuran, toluene, benzene, methylethylketone and dioxane.

17. A method according to the claim 13, wherein the polymerizing reaction is conducted at 50–80° C.

18. A polymer represented by general formula 2

(general formula 2)

wherein, $R_a$, $R_b$ and $R_c$ each represents hydrogen or methyl; $R_1$ represents hydrogen, hydroxy, a substituted or non-substituted straight or branched $C_1$–$C_5$ alkyl, cycloalkyl, alkoxyalkyl or cycloalkoxyalkyl; x, y and z each represents mole fraction of 0.01–0.99; and n represents an integer of 1 to 4.

19. A polymer according to the claim 18, wherein $R_1$ represents methyl.

20. A polymer according to the claim 18, wherein the polymer is poly (tosylmethylacrylamide-hydroxyethylacrylate-methylmethacrylate) and the ratio of x:y:z is 0.3:0.3:0.25.

21. A polymer according to the claim 18, wherein the polymer is poly (tosylmethylacrylamide-hydroxyethylmethacrylate-methylmethacrylate) and the ratio of x:y:z is 0.33:0.35:0.25.

22. A polymer according to the claim 18, wherein the polymer is poly (tosylmethylacrylamide-hydroxypropylacrylate-methylmethacrylate) and the ratio of x:y:z is 0.3:0.33:0.22.

23. A polymer according to the claim 18, wherein the polymer is poly (tosylmethylacrylamide-hydroxypropylmethacrylate-methylmethacrylate) and the ratio of x:y:z is 0.3:0.33:0.25.

24. A polymer according to the claim 18, wherein the polymer is poly (tosylmethylacrylamide-hydroxybutylacrylate-methylmethacrylate) and the ratio of x:y:z is 0.3:0.3:0.3.

25. A polymer according to the claim 18, wherein the polymer is poly (tosylmethylmethacrylamide-hydroxyethylacrylate-methylmethacrylate) and the ratio of x:y:z is 0.3:0.25:0.3.

26. A polymer according to the claim 18, wherein the polymer is poly (tosylmethylmethacrylamide-hydroxyethylmethacrylate-methylmethacrylate) and the ratio of x:y:z is 0.3:0.32:0.3.

27. A polymer according to the claim 18, wherein the polymer is poly (tosylmethylmethacrylamide-hydroxypropylacrylate-methylmethacrylate) and the ratio of x:y:z is 0.3:0.33:0.3.

28. A polymer according to the claim 18, wherein the polymer is poly (tosylmethylmethacrylamide-hydroxypropylmethacrylate-methylmethacrylate) and the ratio of x:y:z is 0.3:0.3:0.3.

29. A polymer according to the claim 18, wherein the polymer is poly (tosylmethylmethacrylamide-hydroxybutylacrylate-methylmethacrylate) and the ratio of x:y:z is 0.3:0.33:0.3.

30. A method for preparing a polymer of claim 18 which comprises polymerizing a tosylalkylacrylamide-type monomer, a hydroxyalkylacrylate-type monomer and an alkylacrylate-type monomer in a solvent in the presence of an initiator as shown in the following reaction equation 2:

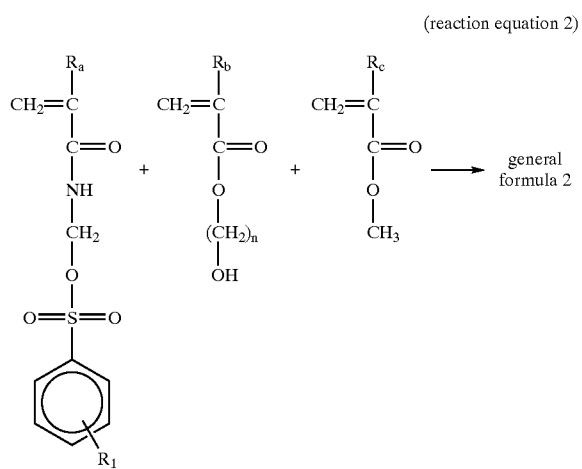

(reaction equation 2)

wherein, $R_a$, $R_b$ and $R_c$ each represents hydrogen or methyl; $R_1$ represents hydrogen, hydroxy, a substituted or non-substituted straight or branched $C_1$–$C_5$ alkyl, cycloalkyl, alkoxyalkyl or cycloalkoxyalkyl; and n represents an integer of 1 to 4; and the mole fraction of each monomer is 0.01–0.99.

31. A method according to the claim 30, wherein $R_1$ represents methyl.

32. A method according to the claim 30, wherein the initiator is selected from the group consisting of 2,2-azobisisobutyronitrile(AIBN), acetylperoxide, laurylperoxide and t-butylperoxide.

33. A method according to the claim 30, wherein the solvent is selected from the group consisting of tetrahydrofuran, toluene, benzene, methylethylketone and dioxane.

34. A method according to the claim 30, wherein the polymerizing reaction is conducted at 50–80° C.

35. An anti-reflective coating composition comprising a polymer of claim 1.

* * * * *

UNITED STATES PATENT AND TRADEMARK OFFICE
CERTIFICATE OF CORRECTION

PATENT NO.    : 6,423,797 B1
DATED         : July 23, 2002
INVENTOR(S)   : Sung-Eun Hong, Min-Ho Jung and Ki-Ho Baik It is certified that error appears in the above-identified patent and that said Letters Patent is hereby corrected as shown below:

Title page,
Item [57], ABSTRACT,
Line 16, the phrase "ultrafine-patters" should read -- ultrafine-patterns --.

Column 3,
Line 65, the term "wavelenth." should read -- wavelength --.

Column 6,
Line 44, the term "Tosylmethylmethacrlamide" should read
-- Tosylmethylmethacrylamide --.

Column 8, lines 6 and 51, Column 9, line 29, Column 10, line 6, Column 11, line 29, Column 12, line 5, Column 13, line 29, Column 14, lines 6 and 51, Column 15, line 29, Column 16, lines 6 and 53, Column 17, line 30, Column 18, lines 6 and 51, Column 19, lines 25 and 65, the term "methylmethacylate" should read -- methylmethacrylate --.

Column 10,
Line 50, the term "hydroxyethylmetacrylate" should read -- hydroxyethylmethacrylate --.

Column 11,
Lines 2-20, chemical formula 8 should read
--
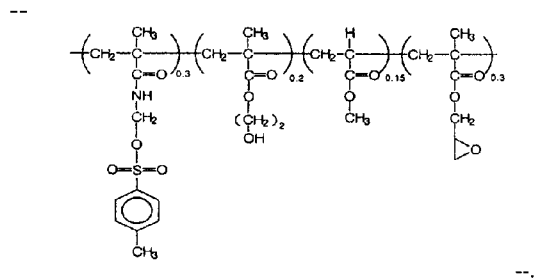
                                                                    --.

Line 33, please delete the space between numbers 1 and 5 in the parenthesis.

UNITED STATES PATENT AND TRADEMARK OFFICE
CERTIFICATE OF CORRECTION

PATENT NO. : 6,423,797 B1
DATED : July 23, 2002
INVENTOR(S) : Sung-Eun Hong, Min-Ho Jung and Ki-Ho Baik It is certified that error appears in the above-identified patent and that said Letters Patent is hereby corrected as shown below:

Column 16,
Line 52, the term "tosylmethylacrlyamide" should read -- tosylmethylacrylamide --.

Column 17,
Line 45, please delete the space between numbers 7 and 5 before the period.

Column 21,
Line 60, please replace the term "claims" with the term -- claim --.

Signed and Sealed this

Twentieth Day of May, 2003

JAMES E. ROGAN
*Director of the United States Patent and Trademark Office*